(12) United States Patent
Phillips et al.

(10) Patent No.: US 7,326,231 B2
(45) Date of Patent: Feb. 5, 2008

(54) DEVICE FOR THE REPAIR OF ARTERIES

(75) Inventors: Peter Phillips, Milton Park (GB); Duncan Keeble, Milton Park (GB)

(73) Assignee: Anson Medical Limited (GB)

( * ) Notice: Subject to any disclaimer, the term of this patent is extended or adjusted under 35 U.S.C. 154(b) by 634 days.

(21) Appl. No.: 10/203,074

(22) PCT Filed: Feb. 9, 2001

(86) PCT No.: PCT/GB01/00551

§ 371 (c)(1),
(2), (4) Date: Aug. 6, 2002

(87) PCT Pub. No.: WO01/58363

PCT Pub. Date: Aug. 16, 2001

(65) Prior Publication Data
US 2003/0033006 A1    Feb. 13, 2003

(30) Foreign Application Priority Data
Feb. 9, 2000    (GB)    ................ 0002970.2

(51) Int. Cl.
*A61B 17/08* (2006.01)
*A61F 2/06* (2006.01)
(52) U.S. Cl. .................. 606/219; 606/153; 623/1.36
(58) Field of Classification Search .......... 606/151, 606/153, 75, 219, 221, 148, 232, 116; 607/126, 607/128; 623/1.36; 24/54, 27, 549, 546; 128/898
See application file for complete search history.

(56) References Cited

U.S. PATENT DOCUMENTS

| 1,109,967 A | * | 9/1914 | Condon | .................. 24/546 |
| 2,108,206 A | * | 2/1938 | Meeker | .................. 606/148 |
| 3,527,223 A | | 9/1970 | Shen | |
| 3,716,058 A | | 2/1973 | Tanner | |
| 3,814,104 A | * | 6/1974 | Irnich et al. | .................. 607/128 |
| 3,868,956 A | * | 3/1975 | Alfidi et al. | .................. 606/194 |
| 4,275,813 A | | 6/1981 | Noiles | |
| 4,317,451 A | | 3/1982 | Cerwin et al. | |
| 4,485,816 A | | 12/1984 | Krumme | |
| 4,590,938 A | | 5/1986 | Segura et al. | |
| 4,921,484 A | | 5/1990 | Hillstead | |
| 5,002,562 A | * | 3/1991 | Oberlander | .................. 606/221 |
| 5,030,224 A | * | 7/1991 | Wright et al. | .................. 606/151 |
| 5,042,707 A | | 8/1991 | Taheri | |

(Continued)

FOREIGN PATENT DOCUMENTS

DE    19711288 A    10/1998

(Continued)

*Primary Examiner*—Julian W. Woo
(74) *Attorney, Agent, or Firm*—Craig A. Fieschko, Esq.; DeWitt Ross & Stevens S.C.

(57) ABSTRACT

A device is provided for piercing a graft and artery wall in order to retain the graft on the artery. The device has a central section with an abutment surface for contacting the inner wall of the graft and two elongate members with distal ends for contacting the outer wall of the artery when the device is pierced through the graft and artery. The elongate members are biased so as to urge the abutment surface into the graft and retain the graft on the artery.

18 Claims, 3 Drawing Sheets

U.S. PATENT DOCUMENTS

| | | | |
|---|---|---|---|
| 5,192,291 A | 3/1993 | Pannek | |
| 5,192,303 A * | 3/1993 | Gatturna et al. | 606/75 |
| 5,219,358 A | 6/1993 | Bendel et al. | |
| 5,222,971 A | 6/1993 | Willard | |
| 5,263,973 A | 11/1993 | Cook | |
| 5,282,845 A * | 2/1994 | Bush et al. | 607/128 |
| 5,330,490 A | 7/1994 | Wilk | |
| 5,411,522 A * | 5/1995 | Trott | 606/232 |
| 5,413,584 A | 5/1995 | Schulze | |
| 5,531,760 A | 7/1996 | Alwafaie | |
| 5,540,716 A | 7/1996 | Hlavacek | |
| 5,573,543 A | 11/1996 | Astashov et al. | |
| 5,586,983 A | 12/1996 | Sanders et al. | |
| 5,618,311 A | 4/1997 | Gryskiewicz | |
| 5,632,746 A | 5/1997 | Pyka | |
| 5,720,755 A | 2/1998 | Dakov | |
| 5,820,628 A | 10/1998 | Middleman et al. | |
| 5,893,856 A * | 4/1999 | Jacob et al. | 606/151 |
| 5,941,890 A | 8/1999 | Boehm et al. | |
| 5,984,949 A | 11/1999 | Levin | |
| 5,990,378 A | 11/1999 | Ellis | |
| 6,071,292 A | 6/2000 | Makower et al. | |
| 6,093,205 A | 7/2000 | McLeod et al. | |
| 6,113,611 A | 9/2000 | Allen et al. | |
| 6,132,438 A | 10/2000 | Fleischman et al. | |
| 6,190,401 B1 | 2/2001 | Green et al. | |
| 6,200,330 B1 | 3/2001 | Benderev et al. | |
| 6,228,055 B1 * | 5/2001 | Foerster et al. | 606/116 |
| 6,273,903 B1 | 8/2001 | Wilk | |
| 6,287,315 B1 | 9/2001 | Wijeratne et al. | |
| 6,334,867 B1 | 1/2002 | Anson | |
| 6,419,686 B1 | 7/2002 | McLeod et al. | |
| 6,447,524 B1 | 9/2002 | Knodel et al. | |
| 6,451,034 B1 | 9/2002 | Gifford et al. | |
| 6,485,496 B1 | 11/2002 | Suyker et al. | |
| 6,749,622 B2 * | 6/2004 | McGuckin et al. | 606/151 |
| 6,994,713 B2 | 2/2006 | Berg et al. | |
| 2005/0165305 A1 * | 7/2005 | Foerster et al. | 600/431 |

FOREIGN PATENT DOCUMENTS

| | | |
|---|---|---|
| EP | 0820729 | 1/1998 |
| FR | 2725126 A | 4/1996 |
| FR | 2746292 | 9/1997 |
| WO | 92/05828 A1 | 4/1992 |
| WO | WO 9608208 A1 * | 3/1996 |
| WO | 98/02100 A1 | 1/1998 |
| WO | 99/00074 A1 | 1/1999 |
| WO | 99/07292 A1 | 2/1999 |
| WO | 99/37242 A1 | 7/1999 |
| WO | 00/07506 A2 | 2/2000 |
| WO | 01/30269 A1 | 5/2001 |

* cited by examiner

DEVICE FOR THE REPAIR OF ARTERIES

This application is the U.S. National Stage entry under 35 U.S.C. § 371 of PCT/GB01/00551, filed Feb. 9, 2001.

FIELD OF THE INVENTION

The present application relates to a device for retaining a graft on an artery, and in particular to a device which can be used surgically to join living tissue or to attach graft material to living tissue. More specifically, it can be used to join a vascular graft to an artery wall, preferably by minimally invasive or endolumenal means.

BACKGROUND OF THE INVENTION

WO 92/05828 discloses a wire-form suture which comprises an open wire ring, the ends of which have been arranged to overlap. The wire-formed ring can be fully or partially straightened, one end sharpened and the whole device driven through adjoining tissues. The wire has a spring or shape memory characteristic which causes it to re-form into a ring shape when in place thereby drawing together the tissues.

An improvement to this design is disclosed in WO 00/07506 (in the name of the present applicant—published after the priority date of the present application), in which a pair of joined wires have a shape memory which causes them to form an 'H' shape upon deployment. This shape has the advantage of symmetry which ensures that the orientation of the device remains stable after implementation. It also has the advantage that the overall width of the device increases after implantation. This reduces the possibility of the device's pulling out from its implantation site. Both of these advantages are particularly important in the critical application of intra-arterial implantation.

A requirement of the design disclosed in WO 00/07506 is that the part of the device where the wires are attached to each other is intended to lie within the wall of the artery and the graft with the divided parts of the device projecting beyond the artery walls and graft on both the lumenal and the visceral sides. A consequence of this requirement is that the paired wires must remain in contact with each other along their lengths while they pass through the artery and graft. If they do not, then the device may not pass fully through the structures or the device may remove a core of material (due to its increased width). This constrains the design of an appropriate delivery system and can increase the risk of misplacement of the device. Such misplacement could have serious consequences for a patient.

SUMMARY OF THE INVENTION

According to a first aspect of the present invention, there is provided a device for retaining a graft on an artery, which device comprises a central section having an abutment surface and two elongate members extending from the central section, the elongate members being resiliently biased into a open configuration in which the ends of the elongate members distal from the central section are spaced apart from one another, wherein the elongate members can be moved against said bias into a closed configuration in which said distal ends are closer together than in the open configuration, wherein said distal ends are adapted to pierce the graft and the artery wall when the device is in the lumen of the artery, so that the elongate members can be urged through the graft and artery wall in order to bring the abutment surface into contact with the graft, such that in use the graft is retained on the artery between said abutment surface and the distal ends of the elongate members with the resilient bias of the elongate members urging the abutment surface against the graft.

By graft is meant any material used to repair or support damaged or weak conduits within a living organism, including arteries and veins. The graft may be formed from nature tissue or from woven, moulded or extruded synthetic polymeric or elastomeric materials and may be tubular or flat (i.e. a patch). It may include a stent i.e. may be a stent-graft.

The provision of an abutment surface which remains inside the lumen of the artery has the advantage that the elongate members can move apart from each other into the open configuration as they advance through the graft and artery walls, because there is not the risk that a core of graft or artery will be removed as in the prior art. In a particularly preferred embodiment, there are no projections from the central section which remain in the lumen of the artery when the device is in place, so that minimal obstruction is caused to fluid flow through the artery.

In a preferred embodiment the device is formed from elastic wire, the central section being formed from a loop in the wire, wherein an external surface of the loop forms the abutment surface. The loop is preferably formed from half to two, and most preferably about one and a half, turns of said wire.

The provision of a loop is an efficient and elegant mechanical solution, in that it enables the device to be formed from a single piece of wire; it provides for the biasing of the elongate members; it provides an abutment surface which curves away from the graft wall to reduce damage; and it provides a place on the device for the attachment of a suture to enable the device to be repositioned within the artery lumen.

In a particularly preferred embodiment, the loop is formed so that moving the elongate members into the closed position closes the loop. This increases the resilient bias of the elongate members and avoids unwrapping the loop when the device is moved into the closed configuration.

The elongate members may be disposed approximately on the same plane when the device is in the open configuration, and the construction of the device is preferably such that the minimum angle between a vector from the central section to one of said distal ends and a vector from the central section to the other of said distal ends when the device is in the open configuration is from 150 to 180°. Clearly, when the device is in use pierced through the graft and artery, it is likely to be disposed somewhere between the closed and the open configurations, depending on the thickness of the graft and artery walls.

According to a second aspect of the present invention, there is provided a method for retaining a graft on an artery, comprising providing a device as defined above, moving the elongate members into the closed configuration, conveying the device along the artery until it is inside the graft, driving the distal ends of the elongate members into the graft and then the artery such that the elongate members move away from the closed configuration and towards the open configuration as they pierce the graft and artery, and continuing to drive the device through the graft and artery until the abutment surface abuts the graft wall, whereby the graft is retained on the artery by the device. The device is preferably conveyed along the artery in a catheter with the distal ends of the elongate members leading and the central section following.

The improved design disclosed here reverses the requirement of PCT/GB99/02544 so that the paired members of the device are separate as they pass through the walls of both the graft and the artery and they remain separate on the visceral side of the artery. A further improvement is that the part of the device where the paired members are connected lies within the lumen of the artery rather than in its wall. As a consequence there is no requirement of the delivery system to retain the paired members of the device in contact. Neither is there a requirement for a single, large hole to be made in the wall of the artery in which the joined part of the paired members can lie. In these ways the improved design makes successful delivery more likely and reduces the risk of damage to the artery wall.

The device may be constructed from a number of materials including metals and plastics and it may be fabricated from separate components, cut from a single block of material, moulded, cast or otherwise constructed.

Typical dimensions of the preferred embodiment are as follows:

| DIMENSION | MAXIMUM | MINIMUM | PREFERRED |
|---|---|---|---|
| Wire Diameter | 1.0 mm | 0.1 mm | 0.5 mm |
| Wire Length | 50 mm | 4 mm | 25 mm |

As stated above, it is preferred that the device be formed from a single wire with a loop. In an alternative embodiment, however, the device comprises at least two wires which can be constrained to be parallel, each wire having two ends, the wires being joined together at or near to one end by welding, braising or similar means. The second, free ends of the wires are sharpened with a bevel, trocar, bullet, conical, diamond or similar point. The wires may be fabricated from a material which has a spring or thermal or super-elastic shape memory such as nickel/titanium shape memory alloy such that their unconstrained shape is a curved 'Y' or 'gull-wing' shape in which the base of the 'Y' is formed from the joined wires, forming the abutment surface.

Typical dimensions of this embodiment are as follows:

| DIMENSION | MAXIMUM | MINIMUM | PREFERRED |
|---|---|---|---|
| Wire Diameter | 1.0 mm | 0.1 mm | 0.5 mm |
| Weld Length | 5 mm | 1 mm | 2 mm |
| Wire Length | 25 mm | 4 mm | 8 mm |

In use, the device may be pushed through a tube with its sharpened ends arranged to emerge first from the tube. The tube constrains the wires of the device to be almost parallel but ensures that the points of the wires are slightly separate before they penetrate the tissue. The device is ejected progressively from the tube and the sharpened tips of the device are driven by spring recoil or thermal shape recovery to become further and further apart as the device emerges from the tube. When used to attach a vascular graft to an artery wall after delivery from within the artery, the device is disposed so that the welded join lies within the lumen of the artery and the sharpened tips of the device have penetrated both the device and the wall of the artery and have curved away from the midline of the device.

The connection between the wires can include a sleeve which supplies strength, radio-opacity and a mechanical stop to prevent the device from passing through the wall of the artery.

BRIEF DESCRIPTION OF THE DRAWINGS

A number of preferred embodiments of the present invention will now be described with reference to the accompanying drawings, in which.

DETAILED DESCRIPTION OF PREFERRED EMBODIMENTS OF THE INVENTION

Figure 1A:
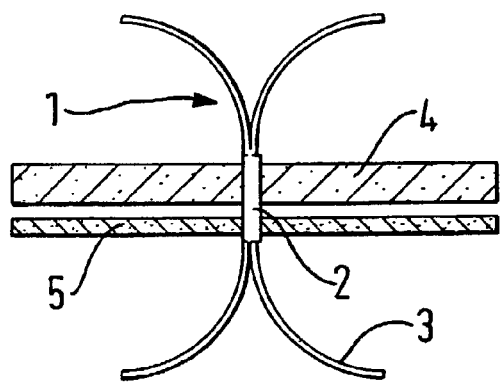
FIG. 1 depicts schematically the prior art device of PCT/GB99/02544.

Turning to the drawings, FIG. 1 shows a prior art fixator 1 (as disclosed in WO 00/07506) having a central section 2 and four legs 3. In FIG. 1A, fixator 1 is correctly positioned across artery wall 4 and graft wall 5, with central section 2 being implanted in artery wall 4. This position arises from the leading legs 3 having passed through graft wall 5 and artery wall 4 together, only separating after they have emerged from artery wall 4.

Figure 1B:
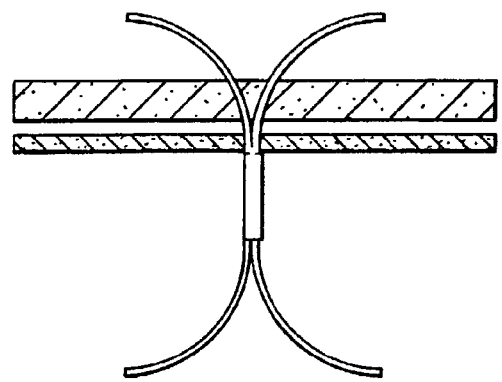

FIG. 1B shows the incorrect placement of fixator 1 resulting from paired legs 3 separating while passing through artery wall 4. It can be seen that, if fixator 1 is advanced any further, a core of material from graft wall 5 and then artery wall 4 will be removed by fixator 1.

Figure 2:
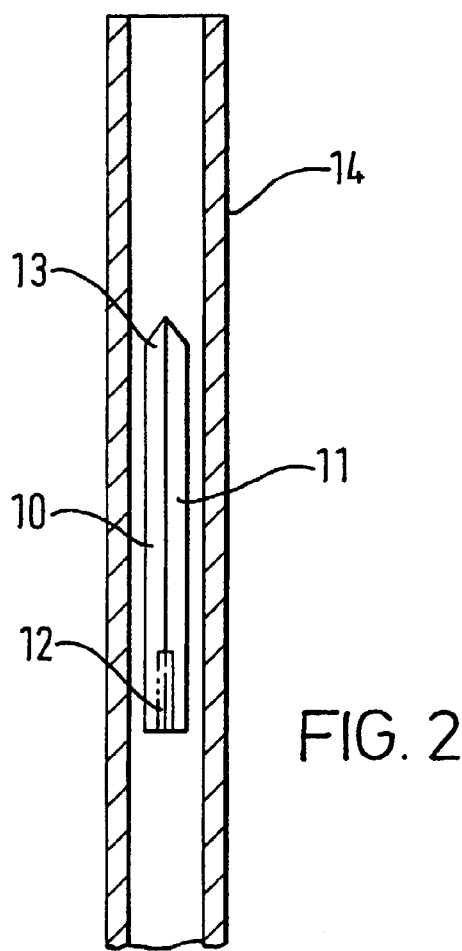
FIG. 2 depicts one embodiment of a device according to the present invention constrained within a delivery tube.
Figure 3:
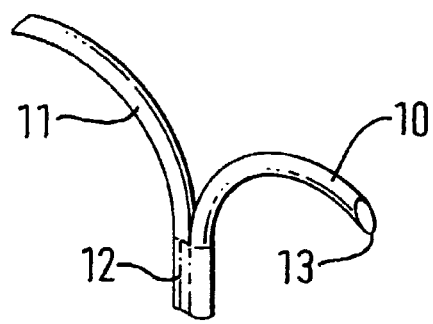
FIG. 3 shows a perspective view of the device of FIG. 2 when open.
Figure 4:
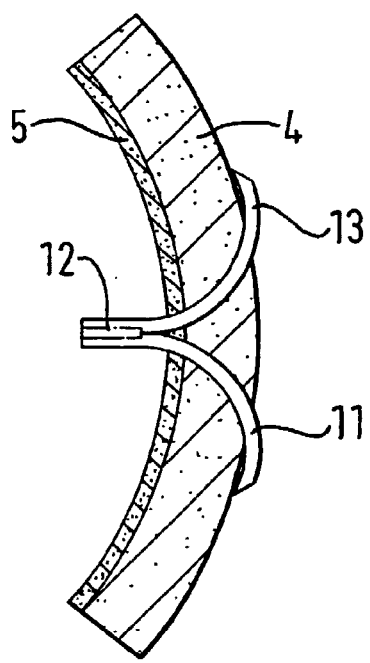
FIG. 4 is a sectional view of the device of FIGS. 2 and 3 implanted through a vascular graft and the wall of an artery.

FIGS. 2 to 4 show an embodiment of the present invention, in which fixator 10 has two legs 11 which are welded together at boss 12 and which terminate at sharpened ends 13. Legs 11 are resiliently biased into the splayed configuration shown in FIG. 3, but can be bent towards each other so as to lie in the generally axial configuration shown in FIG. 2, in which fixator 10 is constrained within delivery catheter 14. FIG. 4 shows fixator 10 in use, with graft 5 retained on artery wall 4 between boss 12 and ends 13 of fixator 10. It can be seen that legs 11 have separated into the open splayed configuration on passing through graft 5 and artery 4.

Figure 5:
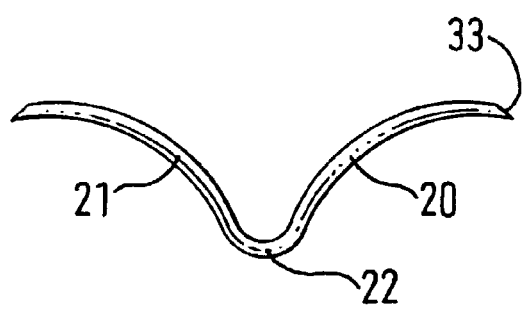
FIG. 5 is a perspective view of an alternative device according to the invention.

FIG. 5 shows an alternative fixator 20 formed from a single resilient wire which is bent into a "gull wing" shape with two legs 21 depending from central section 22 and terminating in sharpened ends 23. It will be appreciated that fixator 20 functions in much the same way as fixator 10 of FIG. 3.

Figure 6:
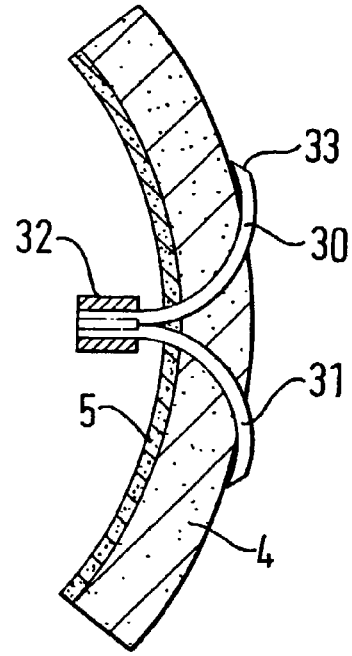
FIG. 6 shows a sectional view of a further alternative device according to the invention implanted through a vascular graft and the wall of an artery.

FIG. 6 shows a further alternative fixator 30 in place retaining graft 5 on artery 4. Fixator 30 has two legs 31 connected at boss 32 by a sleeve made from a radio-opaque material. This enables fixator 30 to be located and tracked by a surgeon. Legs 31 terminate in sharpened ends 33 as before.

Figure 7:
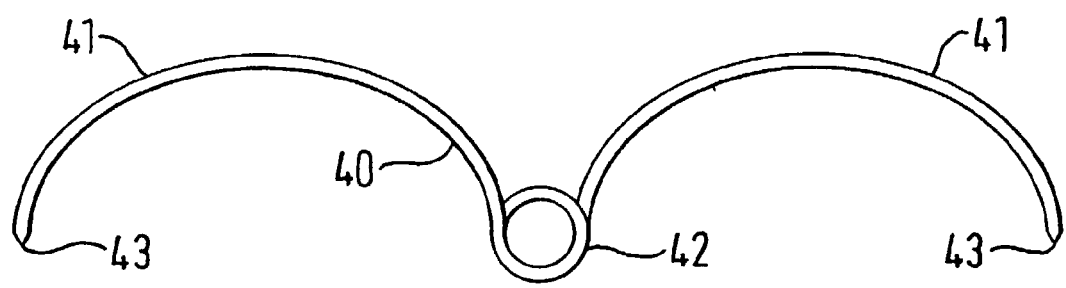
FIG. 7 shows a preferred embodiment of the present invention.
Figure 8:
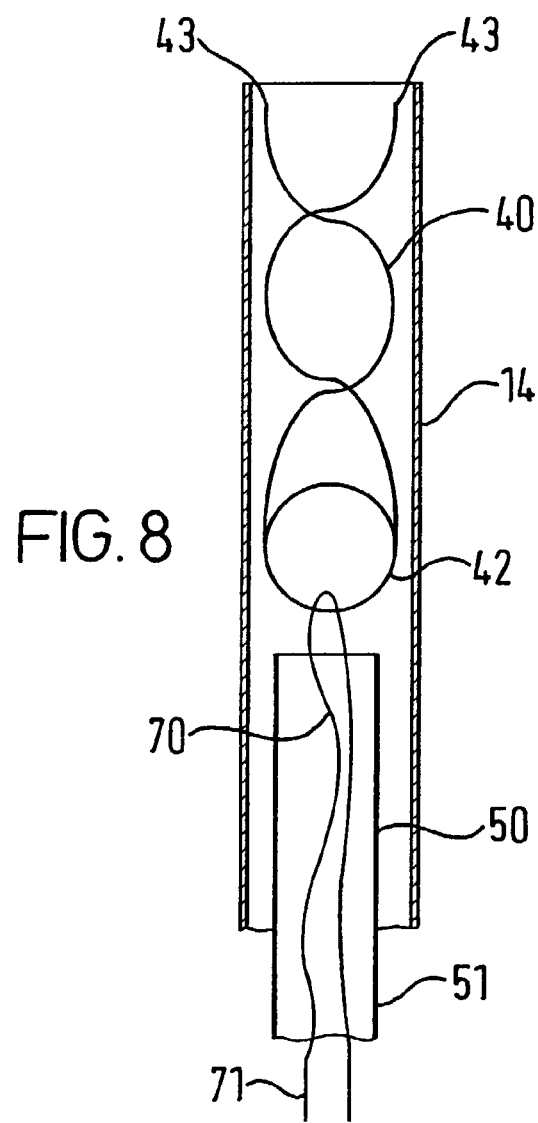
FIG. 8 is a sectional view of the device of FIG. 7 constrained within a delivery tube.

A surgical fixator 40 for attachment of material to body tissue is shown in FIGS. 7 and 8. Fixator 40 is formed from a length of highly elastic wire and comprises a looped portion 42 and two leg members 41. The ends 43 of the leg members are sharpened. Looped portion 42 is a coil of about 1.5 turns. Leg members 41 extend tangentially from each end of looped portion 42 in a generally arcuate form. The centre of legs members 41 are a few millimeters either side of looped portion 42 and at the top of the arc, so that a tangent connecting both arcs is a distance of a few millimeters from the looped portion. The planes of the arc formed by the leg members 41 are generally parallel. The leg members are sharpened to conical points 43. Leg members 41 are generally semi-circular in shape.

Fixator 40 can be elastically deformed so that leg members 41 are folded together and constrained inside a catheter 14 as shown in FIG. 8 with ends 43 of leg members 41 pointing to the distal end of catheter 14. Inside catheter 14 is slideably mounted a positioning tube 50 next to loop 42. The inner bore of positioning tube 50 is smaller than the width of loop 42, so that loop 42 cannot enter positioning tube 50. Also, positioning tube 50 is longer than catheter 14, and can be moved by adjusting the position of the end 51. A length of flexible suture 70 is threaded through loop 42 and positioning tube 50, with two ends suture 70 protruding from positioning tube 50 and connecting together to form a handle 71. The position of fixator 40 relative to catheter 14 can be adjusted by a combination of pushing on positioning tube 50 and pulling on handle 71.

Fixator 40 is used to fix two sheet materials together by positioning the distal end of catheter 14 against and substantially perpendicular to the two materials. Fixator 40 is advanced through catheter 14 by pushing positioning tube 50, until tips 43 of legs 41 protrude and penetrate the materials producing a small aperture. Fixator 40 is then advanced further, and legs 41 will travel through the aperture. Once through the materials legs 41 will resume their arcuate form (the open configuration). The two materials are then retained together between loop 42 on one side and ends 43 of legs 41 on the other side. Suture 70 is removed by pulling one of its ends.

The invention claimed is:

1. A method for retaining a graft on an artery comprising:
  a. providing a graft retention device comprising:
    i. a central section having an abutment surface, and
    ii. only two elongate members extending from the central section, the elongate members being resiliently biased into a open configuration in which the elongate members have a generally arcuate form curved away from each other so that the ends of the elongate members distal from the central section are spaced apart from one another,
  wherein:
    (1) the elongate members can be moved against said bias into a closed configuration in which said distal ends are closer together than in the open configuration,
    (2) said distal ends are adapted to pierce a graft on an artery wall when the device is in the lumen of the artery, so that the elongate members can be urged through the graft and artery wall, moving apart as they do so into the open configuration, in order to bring the abutment surface into contact with the graft,
  such that in use the graft is retained on the artery between said abutment surface and the distal ends of the elongate members with the resilient bias of the elongate members urging the abutment surface against the graft,
  b. moving the elongate members into the closed configuration,
  c. conveying the device along the artery to a locus of the graft wall,
  d. driving the distal ends of the elongate members into the graft and then the artery such that the elongate members move away from the closed configuration and towards the open configuration as they pierce the graft and artery, and
  e. continuing to drive the device through the graft and artery until the abutment surface abuts the graft wall, whereby the graft is retained on the artery by the device.

2. A method as claimed in claim 1, wherein the device is conveyed along the artery in a catheter with the distal ends of the elongate members leading and the central section following.

3. A method as claimed in claim 1, comprising the additional steps of attaching a suture to the device prior to conveying the device along the artery and removing the suture after the graft has been retained on the artery by the device.

4. A method as claimed in claim 3, additionally comprising the step of repositioning the device on the graft wall either before or after the graft wall has been pierced by the elongate members by drawing on the suture to move the elongate members towards the closed configuration.

5. The method of claim 1 wherein the central section and the elongate members are formed of a single piece of wire.

6. The method of claim 5 wherein the central section is formed from a loop in the wire.

7. The method of claim 6 wherein the loop is formed from half to two turns of the wire.

8. The method of claim 6 wherein the loop is formed from about one and a half turns of the wire.

9. The method of claim 6 wherein an external surface of the loop forms the abutment surface.

10. The method of claim 6 wherein the loop extends about a through-hole, the through-hole having an axis which extends at least substantially perpendicularly to an axis defined by the elongate members when the elongate members are in their closed configuration.

11. The method of claim 1 wherein the minimum angle between a vector from the central section to one of the distal ends of the elongate members and a vector from the central section to the distal end of the other of the elongate members when the device is in the open configuration is from 150 to 180 degrees.

12. The method of claim 1 wherein the minimum angle between a vector from the central section to one of the distal ends of the elongate members and a vector from the central section to the distal end of the other of the elongate members when the device is in the open configuration is about 180 degrees.

13. The method of claim 1 wherein the graft retention device additionally comprises means for attaching a suture.

14. The method of claim 13 wherein the means is a loop formed in the central section.

15. The method of claim 14 wherein the loop extends about a through-hole, the through-hole having an axis which extends at least substantially perpendicularly to and axis defined by the elongate members when the elongate members are in their closed configuration.

16. The method of claim 1 wherein the elongate members are disposed approximately on the same plane when the device is in the open configuration.

17. The method of claim 1 wherein, in the closed configuration, the elongate members are disposed substantially on an axis, enabling the device to be conveyed along an artery.

18. The method of claim 1 wherein:
a. the central section is formed from a loop in the wire, and
b. the loop extends about a through-hole, the through-hole having an axis which extends at least substantially perpendicularly to an axis defined by the elongate members when the elongate members are in their closed configuration.

* * * * *